United States Patent
Cleland et al.

(10) Patent No.: US 11,685,763 B2
(45) Date of Patent: Jun. 27, 2023

(54) BONE PROTEIN EXTRACTION WITHOUT DEMINERALIZATION

(71) Applicant: Rensselaer Polytechnic Institute, Troy, NY (US)

(72) Inventors: Timothy Paul Cleland, Pflugerville, TX (US); Deepak Vashishth, Glenmont, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 16/289,782

(22) Filed: Mar. 1, 2019

(65) Prior Publication Data

US 2019/0194247 A1     Jun. 27, 2019

Related U.S. Application Data

(62) Division of application No. 15/533,652, filed as application No. PCT/US2015/065239 on Dec. 11, 2015.

(60) Provisional application No. 62/090,612, filed on Dec. 11, 2014.

(51) Int. Cl.
    *C07K 1/14*      (2006.01)
    *A61K 35/32*     (2015.01)

(52) U.S. Cl.
    CPC ............. *C07K 1/145* (2013.01); *A61K 35/32* (2013.01)

(58) Field of Classification Search
    CPC .................................. C07K 1/145; A61K 35/32
    See application file for complete search history.

(56) References Cited

U.S. PATENT DOCUMENTS

2013/0153818 A1*  6/2013  Oyaizu .................. A23L 3/37
                                                   252/70

OTHER PUBLICATIONS

Carbonnaux et al. Relative Effectiveness of Various Anions on the Solubility of Acidic Hypoderma Lineatum Collagenase at Ph 7.2; Protein Science, vol. 4, pp. 2123-2128. (Year: 1995).*
Cleland et al. Empirical Evaluation of Bone Extraction Protocols; Plos One, vol. 7, No. 2, pp. 1-9. (Year: 2012).*
Pruvost et al. Freshly Excavated Fossil Bone Are Best for Amplification of Ancient DNA; PNAS, vol. 104, No. 3, pp. 739-744. (Year: 2007).*
Anonymous. Phosphosafe Extraction Reagent; Novagen User Protocol TB402 Rev.B0105, downloaded from: http://www.emdmillipore.com/US/en/product/PhosphoSafe-Extraction-Reagent.EMD_BIO-71296#anchor_USP on Jun. 8, 2020. (Year: 2005).*
Fujisawa et al. Acidic Bone Matrix Proteins and Their Roles in Calcification; Frontiers in Bioscience, vol. 17, pp. 1891-1903. (Year: 2012).*
Buckley et al. Distinguishing Between Archaeological Sheep and Goat Bones Using a Single Collagen Peptide; Journal of Archaeological Science, vol. 37, pp. 13-20. (Year: 2010).*
Jiang et al. Method Development of Efficient Protein Extraction in Bone Tissue for Proteome Analysis; Journal of Proteome Research, vol. 6, pp. 2287-2294. (Year: 2007).*
Embery et al. The Isolation and Detection of Non-Collagenous Proteins From the Compact Bone of teh Dinosaur Iguanodon; Connective Tissue Research, vol. 41, No. 3, pp. 249-259. (Year: 2000).*

* cited by examiner

*Primary Examiner* — Melissa L Fisher
*Assistant Examiner* — Paul C Martin
(74) *Attorney, Agent, or Firm* — Murtha Cullina LLP; Anthony P. Gangemi

(57) ABSTRACT

Embodiments of the invention relate generally to protein extraction and, more generally, to bone protein extraction methods that do not require demineralization. In one embodiment, the invention provides a method comprising: mixing a bone sample and a quantity of an extraction buffer comprising: ammonium phosphate dibasic; or ammonium phosphate dibasic and ammonium bicarbonate; or ammonium phosphate dibasic, ammonium bicarbonate, and guanidine HCl; or sodium phosphate dibasic and sodium bicarbonate; or sodium phosphate dibasic, sodium bicarbonate, and guanidine HCl; or potassium phosphate dibasic and potassium bicarbonate; or potassium phosphate dibasic, potassium bicarbonate, and guanidine HCl; and incubating the bone sample/extraction buffer mixture.

4 Claims, 8 Drawing Sheets

BONE PROTEIN EXTRACTION WITHOUT DEMINERALIZATION

CROSS-REFERENCE TO RELATED APPLICATION

This application is a divisional of U.S. patent application Ser. No. 15/533,652, filed Jun. 6, 2017, which is a national stage filing of International Patent Application No. PCT/US2015/065239, filed Dec. 11, 2015, which claims the benefit of U.S. Provisional Application Ser. No. 62/090,612, filed Dec. 11, 2014, which is incorporated herein by reference in its entirety.

STATEMENT REGARDING FEDERALLY SPONSORED RESEARCH OR DEVELOPMENT

This invention was made with government support under grant no. R01 AR049635 awarded by the National Institutes of Health. The government has certain rights in the invention.

BACKGROUND

Bone is a mineralized tissue. As such, extracting proteins from bone typically requires a demineralization step. Such steps are slow (many take days to weeks to perform) and negatively impact subsequent extraction of the proteins. Specifically, demineralization breaks down proteins by hydrolysis. This reduces not only the total protein content recovered from bone samples, but also the types of proteins recovered. For example, most demineralization-based extraction methods recover only about 1% of the original bone mass as protein, most of which is composed of collagen I proteins.

Extraction methods that do not involve demineralization have been developed. These have had very low total protein yields, however, typically 3 mg or less of protein per gram of bone.

BRIEF DESCRIPTION OF THE INVENTION

In one embodiment, the invention provides a method comprising: mixing a bone sample and a quantity of an extraction buffer comprising: ammonium phosphate dibasic; or ammonium phosphate dibasic and ammonium bicarbonate; or ammonium phosphate dibasic, ammonium bicarbonate, and guanidine HCl; or sodium phosphate dibasic and sodium bicarbonate; or sodium phosphate dibasic, sodium bicarbonate, and guanidine HCl; or potassium phosphate dibasic and potassium bicarbonate; or potassium phosphate dibasic, potassium bicarbonate, and guanidine HCl; and incubating the bone sample/extraction buffer mixture.

In another embodiment, the invention provides an extraction buffer comprising: ammonium phosphate dibasic; or ammonium phosphate dibasic and ammonium bicarbonate; or ammonium phosphate dibasic, ammonium bicarbonate, and guanidine HCl; or sodium phosphate dibasic and sodium bicarbonate; or sodium phosphate dibasic, sodium bicarbonate, and guanidine HCl; or potassium phosphate dibasic and potassium bicarbonate; or potassium phosphate dibasic, potassium bicarbonate, and guanidine HCl.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which.

Figure 1:
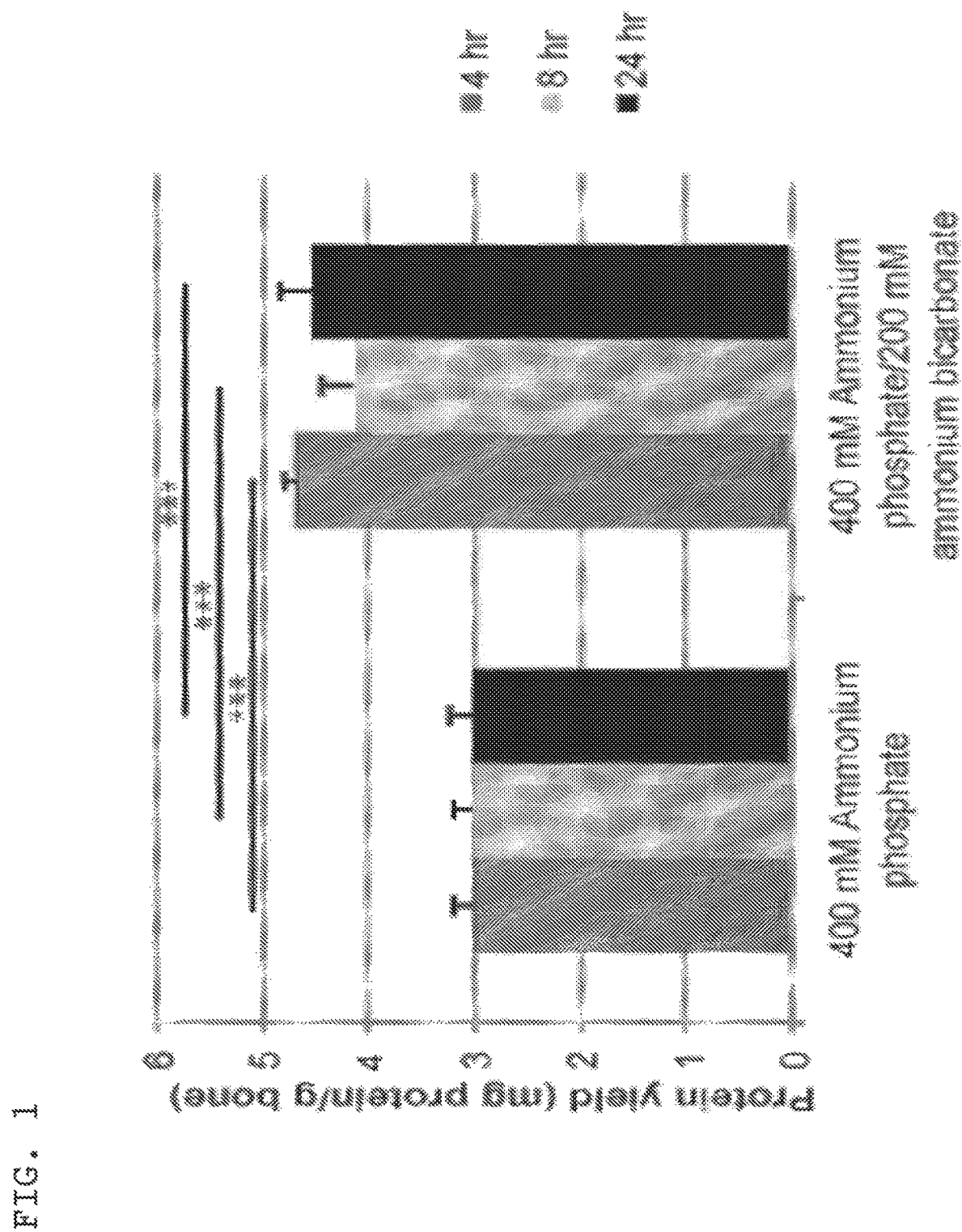
FIG. 1 shows protein yields from bone samples of common origin using different extraction buffers of the invention at four-, eight-, and 24-hour intervals.

It is noted that the drawings of the invention are not to scale. The drawings are intended to depict only typical aspects of the invention, and therefore should not be considered as limiting the scope of the invention.

DETAILED DESCRIPTION OF THE INVENTION

In hydroxyapatite chromatography, proteins are eluted from the hydroxyapatite column with increasing phosphate concentration. Because bone is a composite of hydroxyapatite and protein, the use of higher concentration phosphate buffers similar to the final concentrations used in hydroxyapatite chromatography in bone protein extraction methods allows higher and more complete protein yields than has been achievable using other extraction methods that do not include a demineralization step.

Specifically, extraction buffers comprising ammonium phosphate dibasic (typically at a concentration between about 400 mM and about 1 M) or ammonium phosphate dibasic and ammonium bicarbonate (typically at a concentration of about 200 mM) were employed according to some embodiments of the invention. In other embodiments, extraction buffers comprising ammonium phosphate dibasic, ammonium bicarbonate, and guanidine HCl (at a concentration of about 4M) were employed.

The example below illustrates illustrative methods and extraction buffers according to embodiments of the invention, as well as the results of the mass spectrometry of proteins extracted using these methods and buffers. One skilled in the art will recognize, of course, that various modifications of the methods and extraction buffers described are possible and such modifications are within the scope of the invention.

Tibial cortical bone samples were sampled from seven Caucasian cadavers (23F, 25M, 48M, 56M, 79M, 81F, 82M). All samples were previously diagnosed to be free from metabolic bone diseases, HIV, and hepatitis B. No live human subjects were involved in this research study.

Utilizing phosphate elution principles from hydroxyapatite chromatography, extraction buffers comprising either 400 mM ammonium phosphate dibasic or 400 mM ammonium phosphate dibasic/200 mM ammonium bicarbonate were prepared. To determine differences between the two extraction solutions, a number of initial tests were performed on bone obtained from a 48-year-old male. Bone samples (100 mg each; fragmented to ~1 mm$^3$) were extracted in 600 μL of solutions of 400 mM ammonium phosphate dibasic or 400 mM ammonium phosphate dibasic/200 mM ammonium bicarbonate after homogenization using stainless steel beads in a Bullet Blender. Because this is a tube based homogenization method, particle size was not measured. Aliquots were taken at 4, 8, and 24 hrs to evaluate the amount of time necessary to extract protein for each solution.

After initial set of tests, the extraction was repeated on ~50 mg of bone with 400 mM ammonium phosphate, 400 mM ammonium phosphate dibasic/200 mM ammonium bicarbonate, 400 mM ammonium phosphate dibasic/200 mM ammonium bicarbonate/4M guanidine HCl (GuHCl) for a fixed period of 24 hours only. Temperature was varied at 4° C., room temperature, or 75° C. to determine the effects of temperature on extraction. Finally, an additional ~50 mg of bone was extracted at 75° C. with 200 mM ammonium bicarbonate for 24 hrs for comparison to the ammonium phosphate extractions. The 400 mM ammonium phosphate dibasic/200 mM ammonium bicarbonate/4M GuHCl extraction was only tested at 75° C.

After establishing the method with the highest yields, ~50 mg of bone from other cadaveric donors were extracted using the 400 mM ammonium phosphate dibasic/200 mM ammonium bicarbonate extraction for 24 hrs at 75° C. Protein concentration was determined using Coomassie (Bradford) Assay Kit (Thermo-Scientific) with BSA as a protein standard, and all samples were desalted using micro dialysis (3500 MWCO regenerated cellulose; Fisher Scientific) against nanopure water for 4 days.

To evaluate if proteolysis occurs during the 400 mM ammonium phosphate dibasic/200 mM ammonium bicarbonate or the 400 mM ammonium phosphate dibasic/200 mM ammonium bicarbonate/4M GuHCl extraction process, additional 50 mg aliquots of the 48M samples were homogenized with the inclusion of 10 μg/mL Halt™ Protease Inhibitor (Thermo-Scientific) and incubated for 24 hr at 75° C.

The 400 mM ammonium phosphate dibasic extraction and all 400 mM ammonium phosphate dibasic/200 mM ammonium bicarbonate samples were reduced with 10 mM dithiothreitol for 1 hour at room temperature followed by alkylation using 30 mM iodoacetamide for 1 hour in the dark. Proteins were digested overnight with Trypsin Gold (Promega) at 37° C. (1:100 trypsin:protein). Peptide samples were prepared for mass spectrometry using a C18 stage tip. After binding to the C18 disk, samples were washed with 50 μL of 0.1% formic acid and eluted using 20 μL of 80% acetonitrile, 0.1% formic acid. Samples were partially dried in air to remove excess acetonitrile and resuspended to a final volume of 15 L in 0.1% formic acid. Prepared peptides were separated using an Agilent 1200 Series HPLC with a Thermo Scientific BioBasic C18 (2.1 mm ID, 100 mm column length, 5 m particle size) for 75 minutes using either of the following gradients: 1) 2% B 0-5 min, 30% B 5-15 min, 60% B 15-60 min, 95% B 60.01-64 min, 2% B 64.01-75 min or 2) 2% B 0-5 min, 30% B 5-35 min, 60% B 35-60 min, 95% B 60.01-64 min, 2% B 64.01-75 min where A is 0.1% formic acid and B is 100 acetonitrile, 0.1% formic acid. Eluted peptides were characterized on a LTQ-Orbitrap XL (Thermo Scientific). The top 2 peaks were fragmented using either collision induced dissociation (CID) or higher energy collisional dissociation (HCD) in the Orbitrap or the top 5 peaks were fragmented with CID and analyzed in the ion trap. All samples were analyzed by mass spectrometry in triplicate.

Peak lists (mgf) were created in MassMatrix Mass Spectrometric File Conversion Tools v. 3.2. Peak lists were searched against Swissprot and a decoy database using Mascot 2.3 (Matrix Science). The following parameters were set for each search: taxonomy was set to *Homo sapiens*; enzyme=trypsin; up to 3 missed cleavages; variable modifications: carbamidomethyl (C), deamidation (NQ), carboxy (E), oxidation (MKP); static modifications: none; peptide tolerance=10 ppm; fragment tolerance=0.5 Da; and peptide charge=2+, 3+, 4+. Peptide results were filtered using Percolator at p<0.05. Peptides with nonsensical post-translational modifications (e.g., carboxyglutamic acid (Gla) on non-Gla containing proteins) were filtered by hand.

To evaluate the differences in protein yield between extraction types, one-way ANOVA was performed in SigmaStat for Windows 2.03 (SPSS Inc.). Significance was set at p<0.05.

The 400 mM ammonium phosphate dibasic/200 mM ammonium bicarbonate had a significantly greater yield than 400 mM ammonium phosphate dibasic alone for all times (p<0.001), as shown in FIG. 1. In the figures, * is p<0.05,  is p<0.01, and * is p<0.0001. No variation in yield was observed between times.

Figure 2:
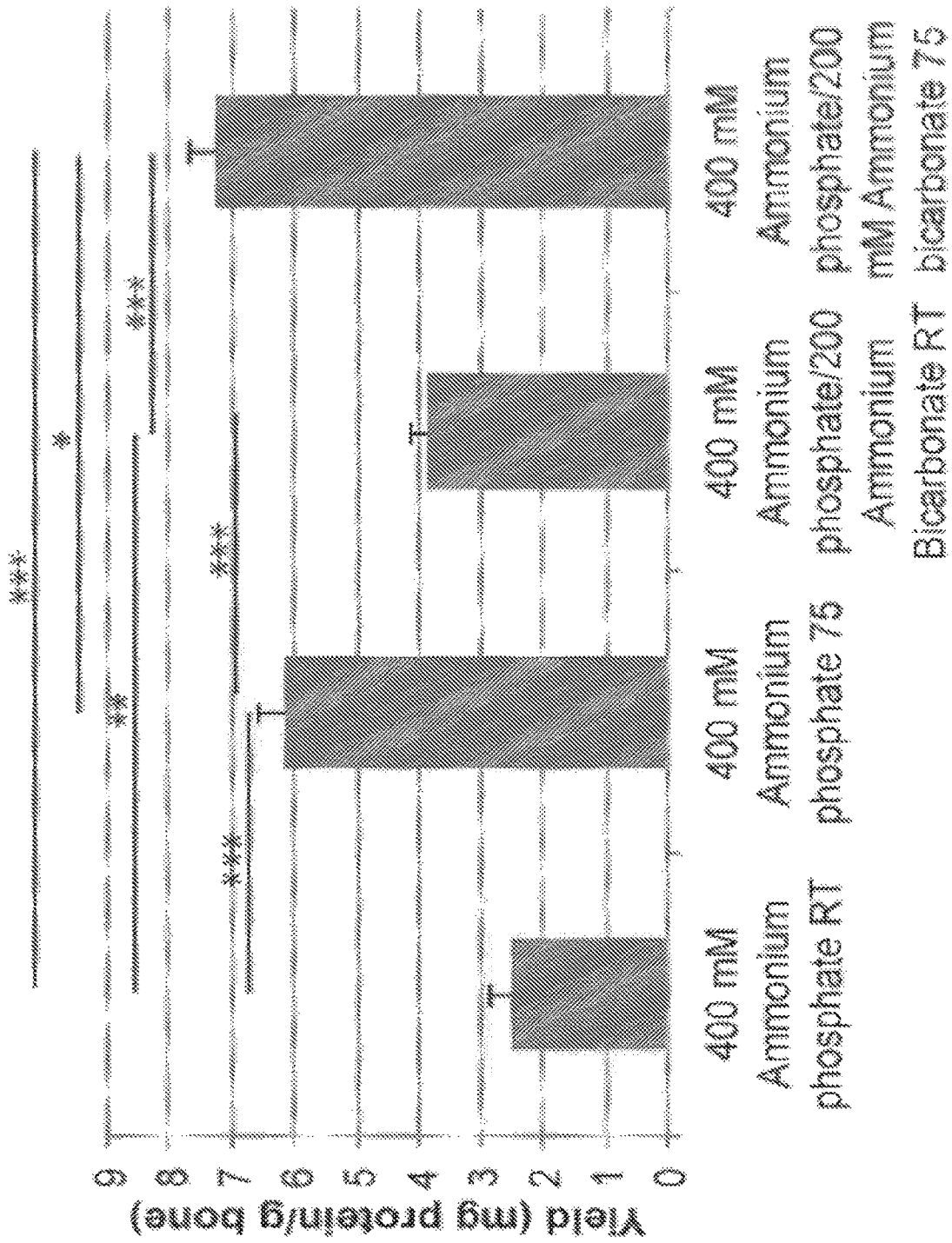
FIG. 2 shows protein yields from bone samples of common origin using different extraction buffers of the invention incubated at room temperature and 75° C.
Figure 3:
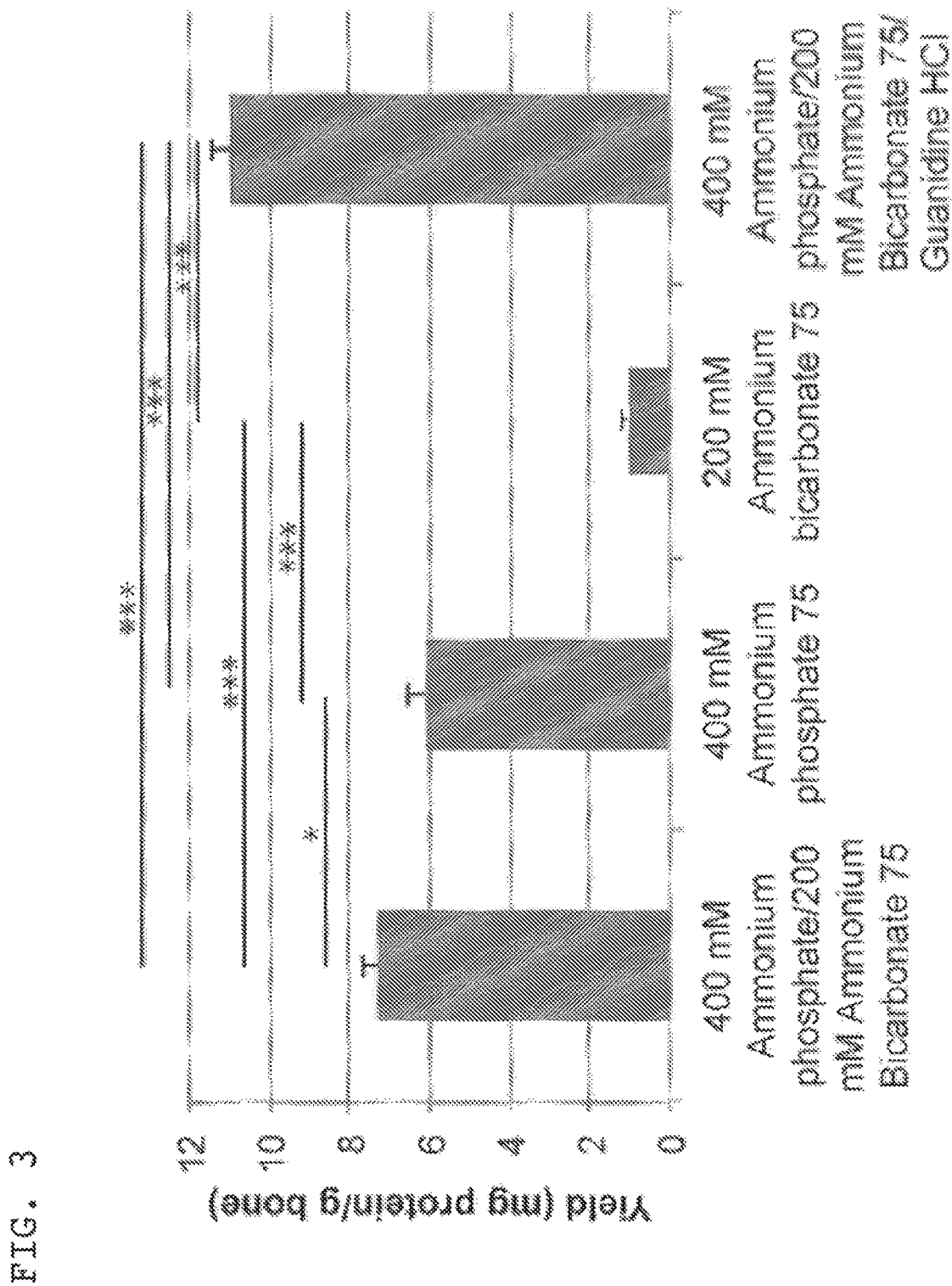
FIG. 3 shows average protein yields for a number of bone samples using different extraction buffers of the invention incubated at 75° C.
Figure 4:
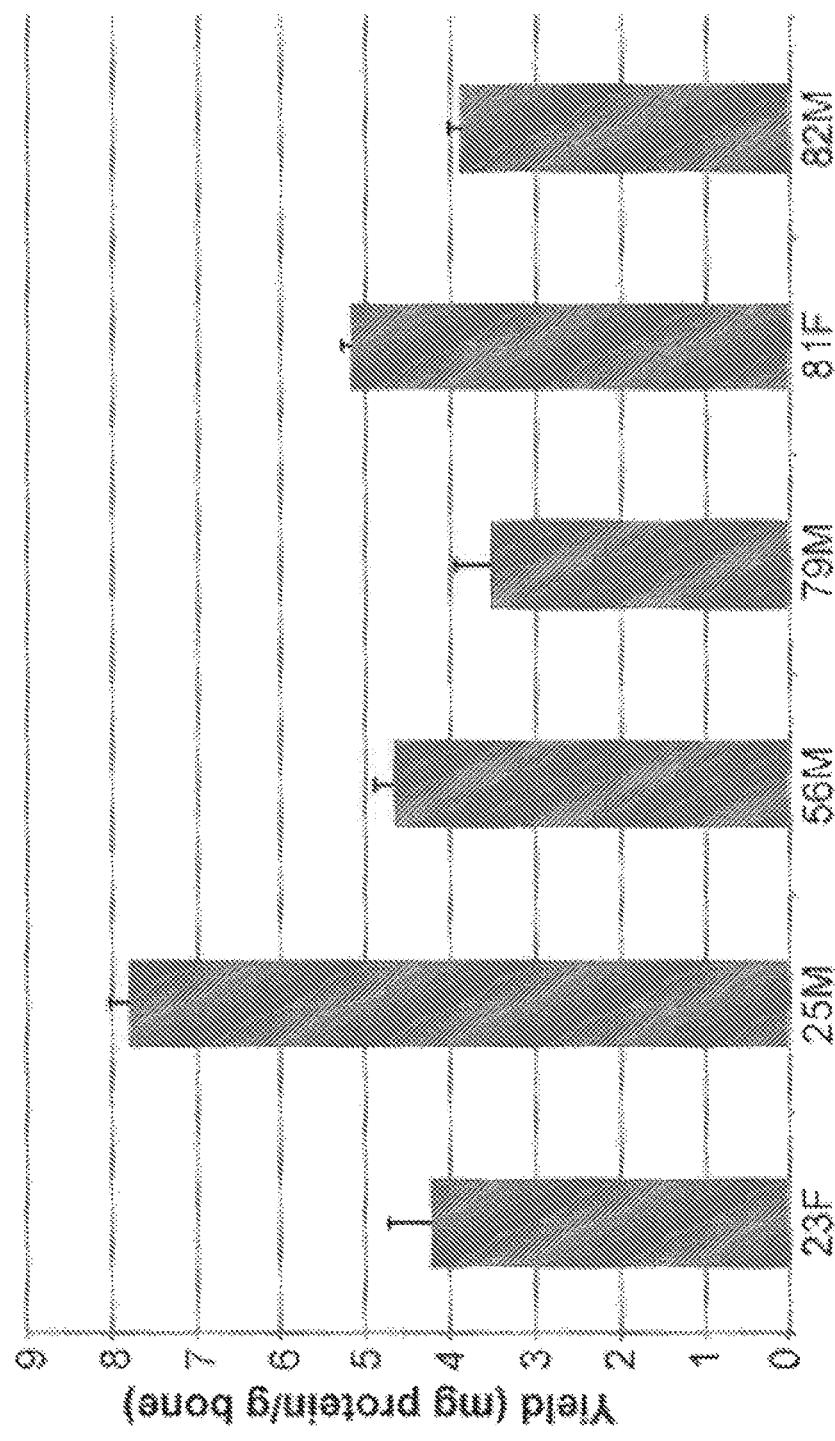
FIG. 4 shows protein yields for a number of bone samples using an extraction buffer comprising 400 mM ammonium phosphate dibasic/200 mM ammonium bicarbonate incubated at 75° C.

Temperature change resulted in a significant increase (p<0.001) in protein concentration for both the 400 mM ammonium phosphate dibasic and 400 mM ammonium phosphate dibasic/200 mM ammonium bicarbonate solutions (FIG. 2). Very little yield (1.05±0.16 mg of protein/g bone) was detected after extraction with 200 mM ammonium bicarbonate at 75° C. (FIG. 3); much less than either ammonium phosphate extraction (p<0.001). The highest yield was obtained with the 400 mM ammonium phosphate dibasic/200 mM ammonium bicarbonate/4M GuHCl extraction (p<0.001). Extractions from bones obtained from the other cadaveric donors resulted in yields between 3.53±0.42 and 7.79±0.23 mg protein per gram of bone (FIG. 4).

For both extractions from the 48-year-old donor, peptides from collagen I were the most abundantly detected. Osteocalcin and ceruloplasmin were only detected in the 400 mM ammonium phosphate dibasic/200 mM ammonium bicarbonate extractions using the top 2 CID method, and actin, serum albumin, and apolipoprotein A-1 were only detected in the 400 mM ammonium phosphate dibasic extraction also only using the top 2 CID method.

Hemoglobin, vimentin, and fibrinogen gamma chain peptides were detected for both 400 mM ammonium phosphate dibasic and 400 mM ammonium phosphate dibasic/200 mM ammonium bicarbonate. Osteocalcin was detected in the 400 mM ammonium phosphate dibasic extraction when using the top 5 CID fragmentation method.

While as few as four hours of extraction was found sufficient for the 400 mM ammonium phosphate dibasic/200 mM ammonium bicarbonate method, 24 hours was used for the individual ages to maximize the amount and types of protein extracted for mass spectrometry. In all samples for the 400 mM ammonium phosphate dibasic/200 mM ammonium bicarbonate extraction fragmented using the top 5 method, collagen I alpha-2 and alpha-1 were consistently the most abundant and second most abundant protein chains detected, respectively. Osteocalcin was detected by Mascot for all samples.

Several other proteins were also detected (e.g., vitronectin, lumican, biglycan). For all samples, 7.3±2.4 proteins, 939.1±185.8 total peptides, and 128.4±19.1 unique peptides were detected using this extraction and mass spectrometry method. After using protease inhibitors, 9 proteins were identified for the 48M sample whereas only 5 were identified in the non-inhibited sample.

The 400 mM ammonium phosphate dibasic/200 mM ammonium bicarbonate/4M GuHCl extraction resulted in the greatest number of protein identifications (as many at 20 unique accession numbers). Collagen I alpha 1 and 2 and osteocalcin were the highest scoring proteins for this extraction, consistent with the other 400 mM ammonium phosphate dibasic/200 mM ammonium bicarbonate extraction. Other matrix proteins (e.g., lumican, biglycan, collagen III, vitronectin, osteomodulin) were also detected.

A number of useful conclusions may be drawn from the results reported in the example above. First, incubation for as little as four hours using either of the extraction buffers (400 mM ammonium phosphate dibasic or 400 mM ammonium phosphate dibasic/200 mM ammonium bicarbonate) resulted in complete protein yields. That is, as can be seen in FIG. 1, longer incubation times (eight hours or 24 hours) did not increase protein yield using either buffer.

Second, increased temperature alone may be sufficient, in some cases, to achieve acceptable protein yields. Referring to FIG. 2 again, it can be seen that while the 400 mM ammonium phosphate dibasic/200 mM ammonium bicarbonate buffer was consistent in achieving higher yields than the 400 mM ammonium phosphate dibasic buffer at both room temperature and at 75° C., the 400 mM ammonium phosphate dibasic buffer at 75° C. had a higher yield than did the 400 mM ammonium phosphate dibasic/200 mM ammonium bicarbonate at room temperature.

Third, the addition of 200 mM ammonium bicarbonate to the extraction buffer significantly increased protein yield over the use of 400 mM ammonium phosphate dibasic alone. This result was consistent regardless of the temperature at which the bone sample/extraction buffer was incubated, as shown in FIG. 3, or the age of the sample donor, as shown in FIG. 4.

Fourth, the proteins extracted were different for each of these two buffers. Table 1 below shows the proteins detected from the bone sample of the 48 year-old male for all temperatures and incubation times using the 400 mM ammonium phosphate dibasic buffer and the 400 mM ammonium phosphate dibasic/200 mM ammonium bicarbonate buffer.

TABLE 1

| 400 mM ammonium phosphate dibasic | 400 mM ammonium phosphate dibasic/ 200 mM ammonium bicarbonate |
|---|---|
| Actin, aortic smooth muscle | Ceruloplasmin |
| Apolipoprotein A-I | Collagen alpha-1(I) chain |
| Collagen alpha-1(I) chain | Collagen alpha-2(I) chain |
| Collagen alpha-2(I) chain | Fibrinogen gamma chain |
| Fibrinogen gamma chain | Hemoglobin subunit alpha |
| Hemoglobin subunit beta | Hemoglobin subunit beta |
| Histone H2A | Osteocalcin |
| Serum albumin | Vimentin |
| Vimentin | |

Together, these results demonstrate the ability to tailor both the protein yields and protein types to be extracted by varying the composition of the extraction buffer, the incubation temperature, or both.

It must also be recognized that the addition of a denaturing agent (4 M guanidine HCl) did significantly increase the total protein yield over the 400 mM ammonium phosphate/200 mM ammonium bicarbonate alone, as shown in FIG. 3. This also resulted in the extraction of a number of proteins (lumican, biglycan, collagen III, vitronectin, and osteomodulin) that were not extracted using either 400 mM ammonium phosphate alone or 400 mM ammonium phosphate/200 mM ammonium bicarbonate alone. This is a result of an increase in the solubility of matrix proteins that may not be soluble without denaturation and suggests an additional degree of flexibility in tailoring the protein yields and types extracted according to embodiments of the invention.

Osteocalcin and osteomodulin were the only mineral specific proteins detected using the methods and buffers of the invention. However, this result suggests that these methods and buffers can interact with the hydroxyapatite surface sufficiently to dissociate mineral proteins. Osteocalcin was only detected consistently in extractions that employed ammonium bicarbonate, suggesting that bicarbonate can disrupt the carboxyl interaction between osteocalcin and the mineral surface.

The addition of a protease inhibitor allowed for the extraction and identification of additional proteins (e.g., Collagen alpha-1 (XXVIII) chain). This may be critical to the wider characterization of the bone proteome. Protease inhibitors suitable for use in accordance with embodiments of the invention include, for example, sodium fluoride, sodium orthovanadate, sodium pyrophosphage, beta-glycerophosphate, and mixtures thereof.

Table 2 below summarizes some of the proteins extracted using each of four extraction buffers according to various embodiments of the invention. In Table 2, Buffer A comprises 400 mM ammonium phosphate dibasic/200 mM ammonium bicarbonate, Buffer B comprises 400 mM ammonium phosphate dibasic/200 mM ammonium bicarbonate/4 M guanidine HCl, Buffer C comprises 400 mM ammonium phosphate dibasic/200 mM ammonium bicarbonate/10 µg/mL Halt™ protease inhibitor, and Buffer D is 400 mM ammonium phosphate dibasic/200 mM ammonium bicarbonate/4 M guanidine HCl/10 µg/mL Halt™ protease inhibitor.

TABLE 2

| Protein | Buffer A | Buffer B | Buffer C | Buffer D |
|---|---|---|---|---|
| Alpha-1-antitrypsin | | X | X | |
| Alpha-2-macroglobulin | | X | | |
| Basement membrane-specific heparan sulfate proteoglycan core protein | | X | | |
| Biglycan | X | X | X | |
| Chondroadherin | X | X | | X |
| Collagen alpha-1(I) chain | X | X | X | X |
| Collagen alpha-1(III) chain | X | X | | |
| Collagen alpha-1 (V) chain | X | | | |
| Collagen alpha-1 (V) chain/ Collagen alpha-1 (IX) chain | X | | | |
| Collagen alpha-1 (V) chain/ Collagen alpha-2 (XI)/ Collagen alpha-1 (XI) chain | X | | | |
| Collagen alpha-1(XI) chain | | X | | |
| Collagen alpha-1 (XXVIII) chain | | | | X |
| Collagen alpha-2(I) chain | X | X | X | |
| Collagen alpha-2(VI) chain | | X | | |
| Collagen alpha-2 (XI) chain | X | | | |
| Collagen alpha-3(VI) chain | | X | | |
| Collagen alpha-5(IV) chain | | X | | X |

TABLE 2-continued

| Protein | Buffer A | Buffer B | Buffer C | Buffer D |
|---|---|---|---|---|
| Glyceraldehyde-3-phosphate dehydrogenase | X | | | |
| Hemoglobin subunit beta | X | | X | |
| Histone H2A 1-B/E | | X | | X |
| Ig gamma-1 chain C region | X | X | | |
| Ig kappa chain C region | X | X | | X |
| Keratin-associated protein 1-1 | | X | | |
| Lumican | X | X | X | X |
| Myoglobin | X | | | |
| Myosin light chain 1/3, skeletal muscle isoform | X | | | |
| Osteocalcin | X | X | X | X |
| Osteomodulin | | X | | |
| Pigment epithelium-derived factor | | X | | |
| Serum albumin | X | X | X | X |
| Tenascin | | X | | |
| Vimentin | X | | | |
| Vitronectin | | X | X | X |
| Zinc finger protein 197 | X | | | |

Figure 5:
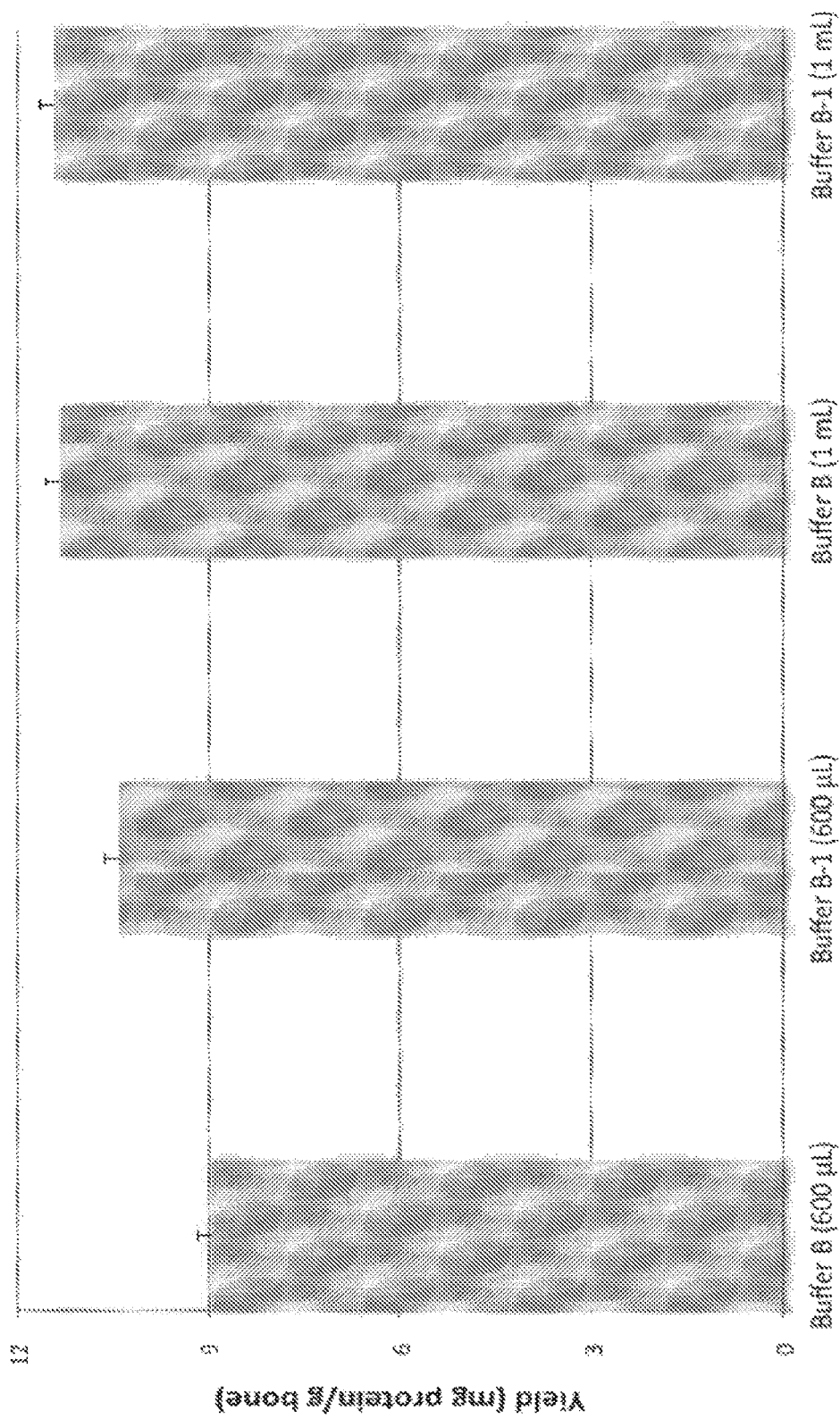
FIG. 5 shows protein yields of extraction buffers according to the invention with varying buffer volumes and phosphate concentrations.

Applicant further found that the volume of extraction buffer for a given mass of bone sample affected the total protein yield. For example, FIG. 5 shows the protein yields for four extractions of bone samples of the same mass and source. In FIG. 5, Buffer B comprises 400 mM ammonium phosphate dibasic/200 mM ammonium bicarbonate/4 M guanidine HCl and Buffer B-1 comprises 1 M ammonium phosphate dibasic/200 mM ammonium bicarbonate/4 M guanidine HCl. As can be seen in FIG. 5, the increased concentration of ammonium phosphate dibasic increased total protein yield using both 600 µL and 1 mL of extraction buffer. At the same time, the 1 mL extractions with both buffers had higher total protein yields than did their 600 µL counterparts.

Figure 6:
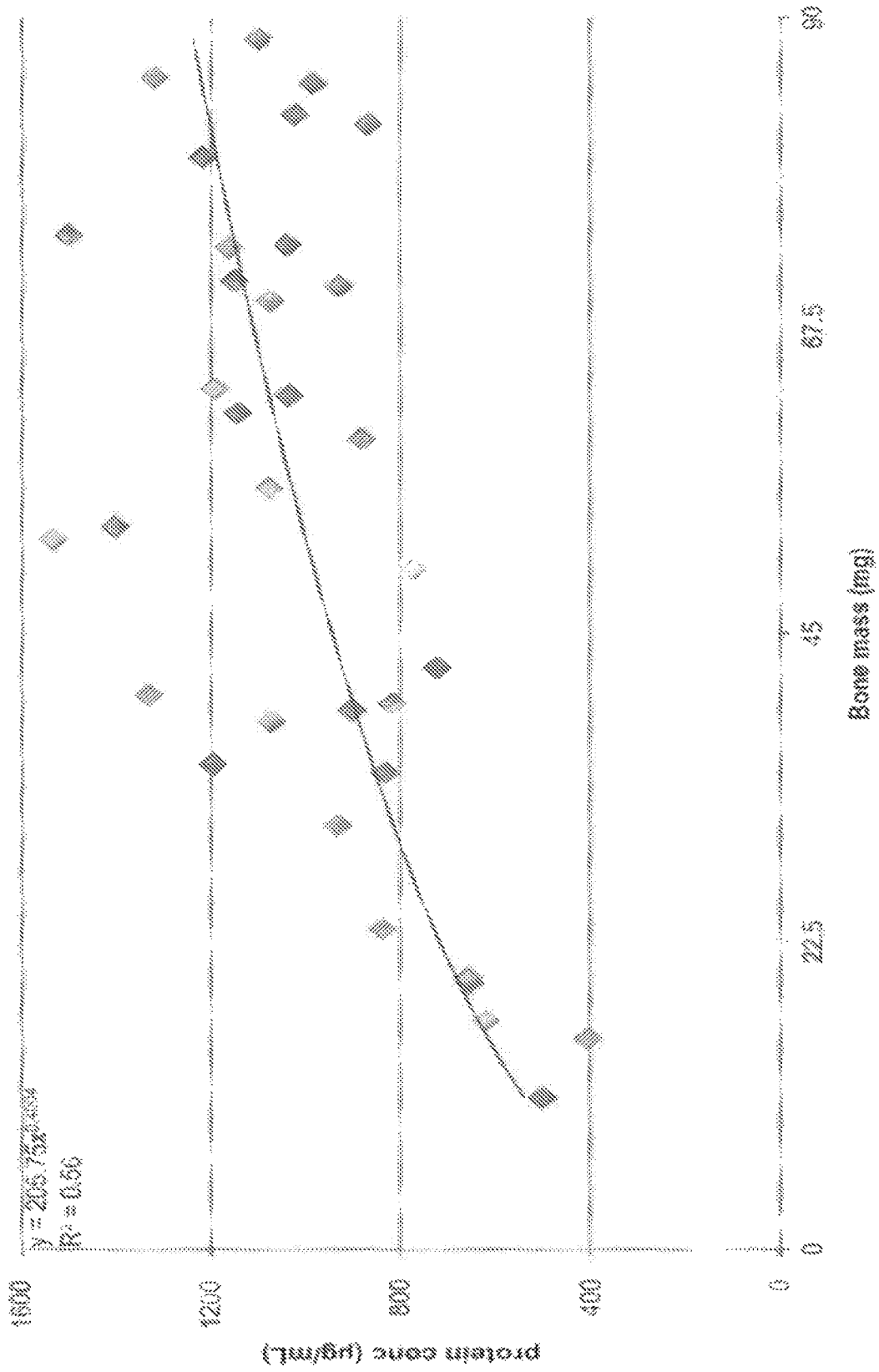
FIG. 6 shows a plot of protein concentration as a function of bone sample mass using extraction buffers according to the invention.

Protein concentration was also found to increase with increasing mass of the bone sample extracted. FIG. 6 shows a plot of protein concentration (kg/mL) as a function of bone mass (mg) for a total of 34 extractions using extraction buffers according to embodiments of the invention. Although not linear, the increase in protein concentration is steady through bone masses of about 90 mg. This suggests that the extraction methods of the invention are effective across a wide range of sample mass.

Figure 7:
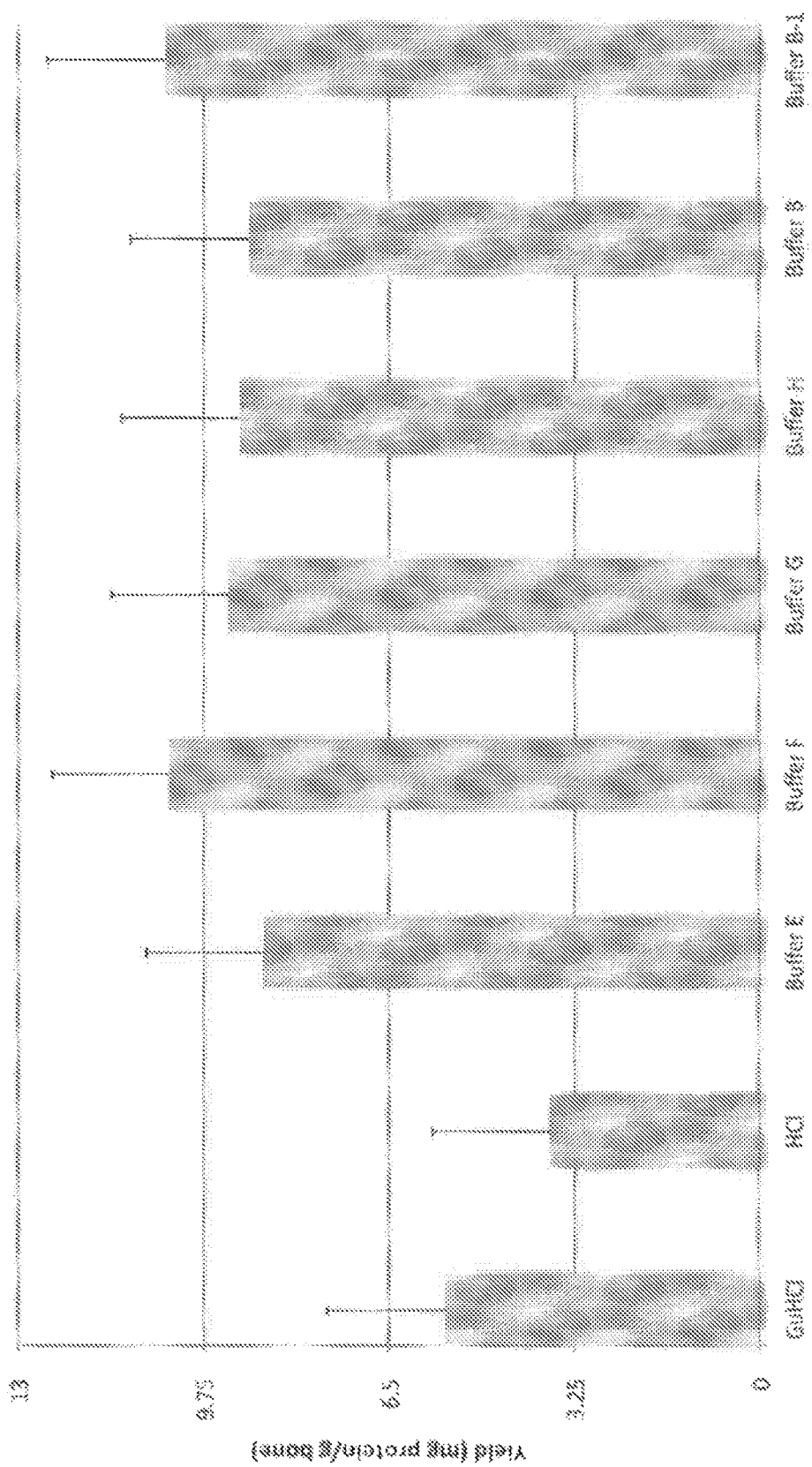
FIG. 7 shows protein yields for various extraction buffers with different cations according to embodiments of the invention.

It was also found that extraction buffers employing other cations were similarly effective in terms of protein yield. FIG. 7, for example, shows the plots of protein yields of six extraction buffers according to the invention as compared to both 4 M guanidine HCl (GuHCl) alone and hydrochloric acid (HCl) alone. HCl is a commonly-used demineralization agent. All extractions were of 60 mg bone samples from the same source. All other parameters were the same among the extractions.

In FIG. 7, Buffer E comprises 400 mM sodium phosphate dibasic/200 mM sodium bicarbonate/4 M guanidine HCl, Buffer F comprises 1 M sodium phosphate dibasic/200 mM sodium bicarbonate/4 M guanidine HCl, Buffer G comprises 400 mM potassium phosphate dibasic/200 mM potassium bicarbonate/4 M guanidine HCl, Buffer H comprises 1 M potassium phosphate dibasic/200 mM potassium bicarbonate/4 M guanidine HCl, and Buffers B and B-1 are as described above with respect to FIG. 5.

As can be seen sodium phosphate dibasic/sodium bicarbonate buffers and potassium phosphate dibasic/potassium bicarbonate buffers resulted in protein yields similar to the ammonium phosphate dibasic/ammonium bicarbonate buffers described above. Guanidine HCl alone and HCl alone resulted in the lowest protein yields.

The types of proteins extracted using other cation-based buffers were similar to those using the ammonium-based buffers described above. Table 3 below summarizes some of the proteins extracted using four different buffers according to embodiments of the invention. In Table 3, Buffer F and Buffer H are as described above with respect to FIG. 7, GuHCl is guanidine HCl alone, and Buffer B-2 comprises 1 M ammonium phosphate dibasic/200 mM ammonium bicarbonate/4 M guanidine HCl/0.015 M phenacylthiazolium bromide (PTB). PTB is reagent that can help enhance protein recovery by breaking advanced glycation end-product crosslinks.

TABLE 3

| Protein | Buffer E | Buffer H | GuHCl | Buffer B-2 |
|---|---|---|---|---|
| Alpha-1-acid glycoprotein 1 | | | X | |
| Alpha-2-HS-glycoprotein | X | X | | X |
| Androgen receptor | | X | | |
| Biglycan | X | X | X | |
| Cathepsin K | | | | X |
| Chondroadherin | X | X | | |
| Collagen alpha-1(I) chain | X | X | X | |
| Collagen alpha-1(II) chain | X | X | X | |
| Collagen alpha-2(I) chain | X | X | X | |
| Decorin | | | X | |
| Dermatopontin | | | X | |
| Fibrinogen gamma chain | | | X | |
| Histone H2A 1-B/E | | | X | |
| Histone H2B type 1-B | | | X | |
| Ig gamma-1 chain C region | | X | X | |
| Ig kappa chain C region | X | | X | |
| Ig lambda chain C region | X | X | X | |
| Lumican | X | X | X | |
| Osteocalcin | X | X | X | |
| Pigment epithelium-derived factor | X | X | X | |
| Prothrombin | X | X | X | |
| Serum albumin | X | X | X | |
| Vitronectin | X | X | X | |

As can be seen in Table 3, Buffer B-2, containing PTB, is the only buffer tested that enabled the extraction of cathepsin K. Guanidine HCl alone enabled the extraction of several proteins that the other buffers did not, although the overall protein yield was lower, as shown in FIG. 7.

Figure 8:
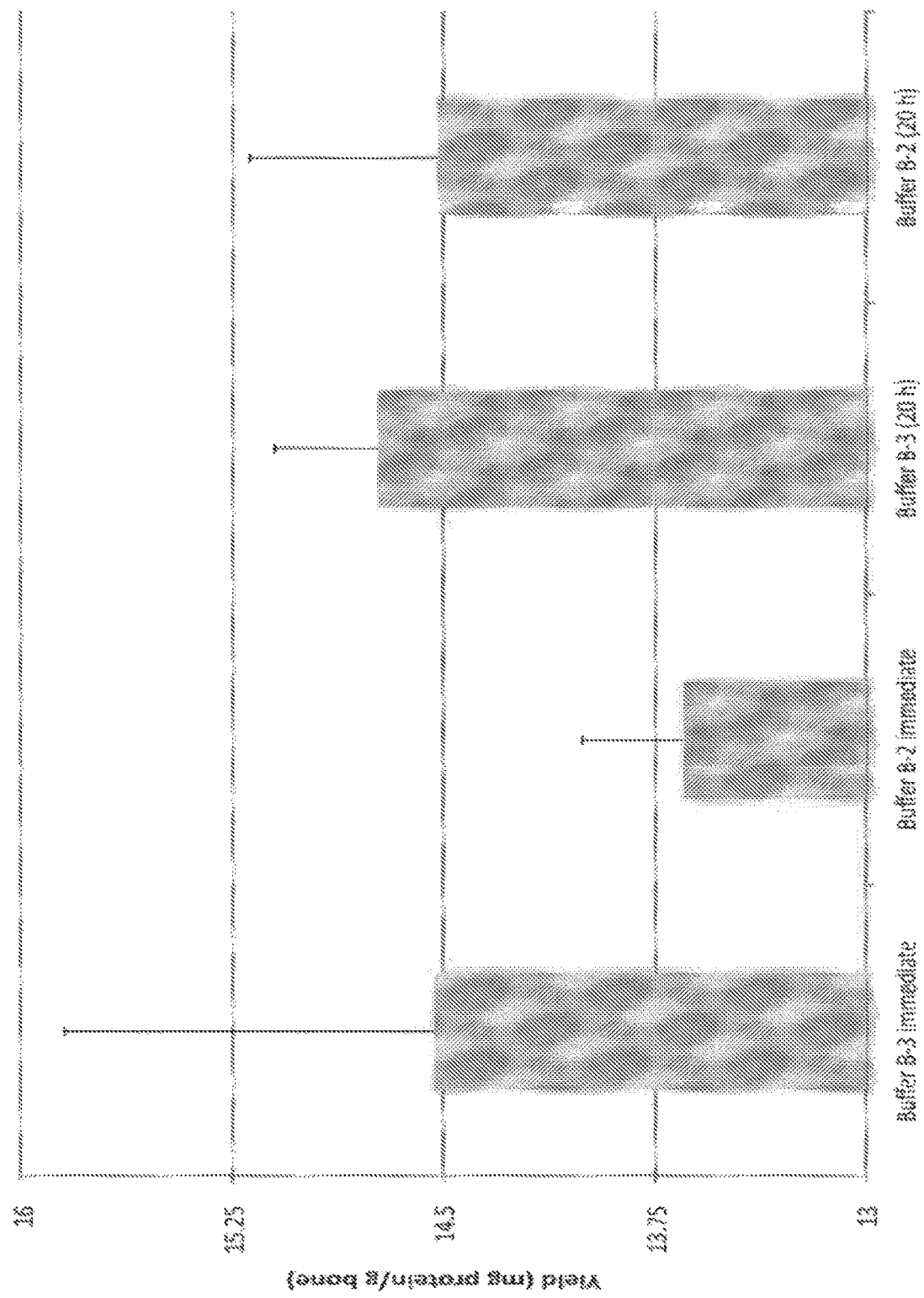
FIG. 8 shows protein yields for extraction buffers including phenacylthiazolium bromide (PTB) according to embodiments of the invention.

The addition of PTB to extraction buffers of the invention results in an increase in total protein yield, particularly with increased incubation, even at a low temperature. FIG. 8, for example, shows plots of total protein yield for two buffers according to the invention, each after two incubation periods. In FIG. 8, Buffer B-3 comprises 400 mM ammonium phosphate/200 mM ammonium bicarbonate/4 M guanidine HCl 0.015 M PTB and Buffer B-2 is as described above with respect to Table 3.

Extractions following incubation for 20 hours at 4° C. increased the total protein yield for both buffers, as compared to yields obtained upon immediate extraction. In both cases, the yields for Buffer B-3 were higher than for Buffer B-2.

As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and also to enable any person skilled in the art to practice the invention, including making and using any devices or systems and performing any related or incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

Although the disclosed subject matter has been described and illustrated with respect to embodiments thereof, it should be understood by those skilled in the art that features of the disclosed embodiments can be combined, rearranged, etc., to produce additional embodiments within the scope of the invention, and that various other changes, omissions, and additions may be made therein and thereto, without parting from the spirit and scope of the present invention.

What is claimed is:

1. A bone protein extraction buffer effective to solubilize matrix proteins from a sample of solid bone, comprising: ammonium phosphate dibasic, ammonium bicarbonate, guanidine HCl, and at least one protease inhibitor, wherein the at least one protease inhibitor is selected from the group consisting of: sodium fluoride, sodium orthovanadate, sodium pyrophosphate, beta-glycerophosphate, and mixtures thereof, wherein the bone protein extraction buffer does not include a demineralization agent, and the extraction buffer includes ammonium phosphate dibasic at a concentration of 400 mM.

2. The extraction buffer of claim 1, wherein the extraction buffer includes ammonium bicarbonate at a concentration of about 200 mM.

3. The extraction buffer of claim 1, wherein the extraction buffer further includes guanidine HCl at a concentration of about 4 M.

4. The extraction buffer of claim 1, further comprising: phenacylthiazolium bromide (PTB).

* * * * *